(12) United States Patent
Lin

(10) Patent No.: US 7,972,767 B2
(45) Date of Patent: Jul. 5, 2011

(54) METHOD FOR CULTURING MESENCHYMAL STEM CELL AND METHOD FOR PRODUCING BIOLOGICAL TISSUE PROSTHESIS

(75) Inventor: Konghua Lin, Hyogo (JP)

(73) Assignee: Olympus Corporation, Tokyo (JP)

( * ) Notice: Subject to any disclaimer, the term of this patent is extended or adjusted under 35 U.S.C. 154(b) by 665 days.

(21) Appl. No.: 11/919,303

(22) PCT Filed: May 9, 2006

(86) PCT No.: PCT/JP2006/309320
§ 371 (c)(1),
(2), (4) Date: Oct. 25, 2007

(87) PCT Pub. No.: WO2006/121043
PCT Pub. Date: Nov. 16, 2006

(65) Prior Publication Data
US 2010/0028997 A1 Feb. 4, 2010

(30) Foreign Application Priority Data

May 9, 2005 (JP) .................................. 2005-135780
Jul. 27, 2005 (JP) .................................. 2005-217835

(51) Int. Cl.
*A01N 1/02* (2006.01)
*A01N 1/00* (2006.01)
*C12N 5/02* (2006.01)

(52) U.S. Cl. ............................... 435/2; 435/1.1; 435/325

(58) Field of Classification Search .......................... None
See application file for complete search history.

(56) References Cited

U.S. PATENT DOCUMENTS 7,052,518 B2 * 5/2006 Irie et al. ..................... 623/23.56
2005/0013804 A1 1/2005 Kato et al.

FOREIGN PATENT DOCUMENTS

| EP | 1 541 182 | 6/2005 |
| WO | WO 99/64566 | 12/1999 |
| WO | WO 00/27996 | 5/2000 |
| WO | WO 01/48147 | 7/2001 |

OTHER PUBLICATIONS

Date-of-Receipt letter to establish the date (Feb. 15, 2010) on which the Search Report was received.
Baksh et al., "Adult human bone marrow-derived mesenchymal progenitor cells are capable of adhesion-independent survival and expansion", Experimental Hematology, vol. 31, No. 8, Aug. 1, 2003, pp. 723-732, XP009086938.
Braccini et al., "Three-Dimensional Perfusion Culture of Human Bone Marrow Cells and Generation of Osteoinductive Grafts", Stem Cells (Miamisburg), vol. 23, No. 8, Sep. 2005, pp. 1066-1072, XP002559990.
Chen, Li-Bo et al., "Differentation of rat morrow mesenchymal stem cells into pancreatic islet beta-cells", World Journal of Gastroenterology, Oct. 15, 2004, pp. 3016-3020, vol. 10, No. 20, XP002363979.
Rangappa, Sunil et al., "Cardiomyocyte-mediated contact programs human mesenchymal stem cells to express cardiogenic phenotype" Journal of Thoracic and Cardiovascular Surgery, Jul. 1, 2003, pp. 124-132, vol. 126, No. 1, XP002411395.
Tropel, Philippe et al., "Isolation and characterisation of mesenchymal stem cells from adult mouse bone marrow", Experimental Cell Research, May 1, 2004, pp. 395-406, vol. 295, No. 2, XP002999367.
Ogura, Naomi et al., "Differentiation of the human mesenchymal stem cells derived from bone marrow and enhancement of cell attachment by fibronectin", Journal of Oral Science, Dec. 2004, pp. 207-213, vol. 46, No. 4, XP002508196.
Lennon DP. et al., "A Chemically Defined Medium Supports In Vitro Proliferation and Maintains the Osteochondral Potential of Rat Marrow-Derived Mesenchymal Stem Cells," Exp. Cell Res., 1995. vol. 219, No. 1, pp. 211 to 222.
European Office Action dated Jun. 10, 2010, issued in European Application No. 06746151.7.
Extended European Search Report dated Dec. 30, 2009 of corresponding European Application No. 09014695.2.

* cited by examiner

*Primary Examiner* — James (Doug) Schultz
(74) *Attorney, Agent, or Firm* — Scully, Scott, Murphy & Presser, P.C.

(57) ABSTRACT

The purpose is to proliferate a mesenchymal stem cell to a sufficient degree while reducing the amount of blood serum contained in a biological tissue progenitor cell to be grafted, and to efficiently differentiate the mesenchymal stem cell into the biological tissue progenitor cell. There is provided a method for culturing a mesenchymal stem cell, comprising: a first culture step of proliferating a mesenchymal stem cell in a medium containing blood serum; and a second culture step of differentiating the mesenchymal stem cell into a biological tissue progenitor cell in a medium containing blood serum at a lower concentration than that in the medium used in the first culture step.

8 Claims, 6 Drawing Sheets

METHOD FOR CULTURING MESENCHYMAL STEM CELL AND METHOD FOR PRODUCING BIOLOGICAL TISSUE PROSTHESIS

TECHNICAL FIELD

The present invention relates to a method for culturing a mesenchymal stem cell and a method for producing a biological tissue prosthesis.

BACKGROUND ART

Mesenchymal stem cells (MSCs) contained in bone marrow fluid, and the like, have multi-differentiation potency to differentiate into a variety of cells such as an osteocyte, a chondrocyte, an adipocyte, a myocyte, a stromal cell, a neurocyte, and a tendon cell, thus attracting attention as a cell source for cell therapy and regenerative medicine. However, only a small amount of mesenchymal stem cells can be collected from the bone marrow fluid and the like. Therefore, for use in clinical treatment, it is important that mesenchymal stem cells collected from bone marrow fluid are isolated following concentration, and proliferated to a large amount in a short time.

As a method for efficiently proliferating mesenchymal stem cells, for example, methods disclosed in Patent Document 1 and Patent Document 2 are known.

In these methods, a fibroblast growth factor is added to a medium as a proliferation stimulant for mesenchymal stem cells.

Moreover, fetal bovine serum or human serum is typically used for a medium used for culturing mesenchymal stem cells.

Moreover, as a method for culturing mesenchymal stem cells in bone marrow fluid after the concentration/isolation thereof, a method is known in which, following centrifugation of the collected bone marrow fluid, the supernatant liquid is removed, the remaining precipitate portion alone is seeded in a culture vessel, and the mesenchymal stem cells are proliferated while they are adhered to the bottom face. In this case, a method for cell culture is proposed in which the seeding density of the mesenchymal stem cells adhered to the bottom face of the culture vessel is adjusted to an appropriate value (for example, refer to Patent Document 3).

Patent Document 1

PCT International Publication No. WO02/22788A1

Patent Document 2

PCT International Publication No. WO01/48147A1

Patent Document 3

Japanese Unexamined Patent Application, Publication No. 2004-254519

DISCLOSURE OF INVENTION

However, it is not preferable that fetal bovine serum is contained in a biological tissue progenitor cell to be grafted into human bodies. Moreover, from the viewpoint of the amount of blood collected from a patient, use of a sufficient amount of human serum is limited in many cases. On the other hand, in order to proliferate a small amount of mesenchymal stem cells collected from a patient to a sufficient number of cells, use of fetal bovine serum or human serum in a medium is essential.

Moreover, when mesenchymal stem cells are to be cultured by adhering them to the bottom face of a culture vessel, since the bottom face area to which the cells can be adhered becomes insufficient as the mesenchymal stem cells proliferate, there is a need to perform a shifting operation into a culture vessel having a larger bottom area or a shifting operation into a plurality of culture vessels (a so-called passage operation). The passage operation involves an operation that peels off the mesenchymal stem cells from the bottom face of the culture vessel using a proteolytic enzyme such as trypsin, which may damage the mesenchymal stem cells. Moreover, since shifting into a plurality of culture vessels is involved, a concern in that the mesenchymal stem cells are brought into contact with some sort of bacteria or dust with a higher probability can also be considered. Furthermore, the passage operation is an operation that peels off mesenchymal stem cells adhered to the bottom face of a culture vessel and then adheres the cells to a new culture vessel in order to continue the culture, and therefore, the passage operation itself takes time, and there is also a concern in that the culture period is prolonged.

The present invention takes the above situation into consideration with an object of providing a method for culturing a mesenchymal stem cell and a method for producing a biological tissue prosthesis, capable of proliferating a mesenchymal stem cell to a sufficient degree while reducing the amount of blood serum contained in a biological tissue progenitor cell to be grafted into a living body, and efficiently differentiating the mesenchymal stem cell into the biological tissue progenitor cell.

Moreover, another object of the present invention is to provide a method for culturing a mesenchymal stem cell capable of eliminating the passage operation so that damage to the mesenchymal stem cell can be reduced, the risk of contamination can be reduced, the culture operation can be simplified so as to shorten the culture period, and proliferation can be efficiently performed so as to thereby reduce the amount of bone marrow collected and alleviate the burden on a patient.

In order to achieve the above objects, the present invention provides the following means.

A first aspect of the present invention is a method for culturing a mesenchymal stem cell, comprising: a first culture step of proliferating a mesenchymal stem cell in a medium containing blood serum; and a second culture step of differentiating the mesenchymal stem cell into a biological tissue progenitor cell in a medium containing blood serum at a lower concentration than that in the medium used in the first culture step.

According to the first aspect of the present invention, in the first culture step, a mesenchymal stem cell is proliferated to a necessary number of cells in a medium containing blood serum due to the effect of the blood serum, and then in the second culture step, the mesenchymal stem cell is differentiated into a biological tissue progenitor cell in a medium containing blood serum at a lower concentration.

As a result of investigation, the present inventor found that, in the differentiation stage of a mesenchymal stem cell into a biological tissue progenitor cell, the differentiation can be rather efficiently performed without blood serum. Accordingly, after the mesenchymal stem cell proliferates to a necessary number of cells, employment of a medium containing blood serum at a lower concentration can allow the mesenchymal stem cell to differentiate into a biological tissue progenitor cell more efficiently than a case, as conventionally performed, where the cell is cultured using a medium containing blood serum at a similar [an equivalent] concentration to that in the medium used for proliferation.

In the first aspect of the present invention, preferably, the concentration of blood serum in the medium in the second culture step is approximately zero.

By so doing, the influence of the blood serum can be eliminated in the second culture step, and the differentiation into a biological tissue progenitor cell can be performed more efficiently.

Moreover, in the first aspect of the present invention, the concentration of blood serum in the medium in the second culture step may be higher than zero.

By so doing, the influence of the blood serum can be made remain in the second culture step. As a result, although the efficiency of differentiation into a biological tissue progenitor cell is slightly decreased compared to the case where the concentration thereof is zero, the proliferation of the mesenchymal stem cell can be continued due to the effect of the blood serum. Accordingly, it is effective for the purpose of continuously supplying biological tissue progenitor cells, since a mesenchymal stem cell can be differentiated into a biological tissue progenitor cell while being proliferated.

In the first aspect of the present invention, the blood serum may be fetal bovine serum, or the blood serum may be human serum.

When fetal bovine serum is used, by setting the concentration of the blood serum in the medium in the second culture step to zero, a biological tissue progenitor cell to be grafted into a living body can be prevented from containing fetal bovine serum.

Moreover, when human serum is used, by reducing the concentration of the blood serum in the medium in the second culture step, the amount of blood serum collected from a patient can be reduced and the burden on the patient can be alleviated.

Furthermore, a second aspect of the present invention is a method for producing a biological tissue prosthesis in which a mesenchymal stem cell is seeded and cultured in a biological tissue supporting material made from a biocompatible material, in the second culture step of any method for culturing a mesenchymal stem cell according to the first aspect described above.

According to the second aspect of the present invention, a biological tissue prosthesis having a reduced concentration of contained blood serum can be produced.

A third aspect of the present invention is a method for culturing a mesenchymal stem cell in which a mesenchymal stem cell is cultured by suspending mesenchymal stem cells and hematopoietic stem cells in a medium, while maintaining the ratio of mesenchymal stem cells to hematopoietic stem cells within a range of 1:10 to 1:100.

According to the third aspect of the present invention, the ratio of mesenchymal stem cells to hematopoietic stem cells is maintained within a range of 1:10 to 1:100. Mesenchymal stem cells are concomitant with a variety of cells in the bone marrow, and the mesenchymal stem cells are also kept in a suspended state. Therefore, it can be inferred that a mesenchymal stem cell can proliferate in a suspended state if it is cultured in a state that is close to an in vivo state. As a result of investigation, it was revealed that, by maintaining the ratio of mesenchymal stem cells to hematopoietic stem cells within the above range, conditions that are similar to in vivo conditions can be achieved even outside a living body, and the mesenchymal stem cells can be efficiently cultured. By so doing, it becomes unnecessary to adhere mesenchymal stem cells to the bottom face of a culture vessel, eliminating the necessity of the passage operation so that damage to the mesenchymal stem cell can be reduced, the risk of contamination can be reduced, the culture operation can be simplified so as to shorten the culture period, and proliferation can be efficiently performed so as to thereby reduce the amount of bone marrow collected and alleviate the burden on a patient.

In the third aspect of the present invention, the arrangement may be set such that the ratio of mesenchymal stem cells to hematopoietic stem cells in the medium is monitored so that a liquid factor for increasing the ratio of hematopoietic stem cells may be added if the ratio of mesenchymal stem cells to hematopoietic stem cells is more than 1/10.

By so doing, if the ratio of mesenchymal stem cells is increased, the liquid factor can be added to increase the ratio of hematopoietic stem cells so that the mesenchymal stem cells can be efficiently proliferated in a state close to an in vivo state. The monitoring of the ratio of mesenchymal stem cells to hematopoietic stem cells is performed by flow cytometry (FACS). For example, the number of mesenchymal stem cells is measured with CD29, CD90, or SH3 serving as a cell surface marker, and the number of hematopoietic stem cells is measured with a Stem-kit (BD) by FACS. This enables the ratio of these cells to be monitored.

In this case, the liquid factor for increasing the ratio of hematopoietic stem cells is preferably made from a mixed solution comprising 1 to 100 ng/mL of SCF (Stem Cell Factor), 1 to 50 ng/mL of IL-3 (Interleukin-3), 1 to 50 ng/mL of IL-6, 1 to 50 ng/mL of IL-10, 10 to 300 ng/mL of FL (Flt-3L), and 1 to 50 ng/mL of TPO (Thrombopoietin).

Moreover, in the third aspect of the present invention, the arrangement may be also set such that the ratio of mesenchymal stem cells to hematopoietic stem cells in the medium is monitored so that a liquid factor for increasing the ratio of mesenchymal stem cells may be added if the ratio of hematopoietic stem cells to mesenchymal stem cells is more than 100.

By so doing, if the ratio of hematopoietic stem cells is increased, the liquid factor can be added to increase the ratio of mesenchymal stem cells so that the mesenchymal stem cells can be efficiently proliferated in a state close to an in vivo state.

In this case, the liquid factor for increasing the ratio of mesenchymal stem cells is preferably made from a mixed solution comprising 1 to 100 ng/mL of PDGF (Platelet-Derived Growth Factor), 1 to 100 ng/mL of bFGF (Basic Fibroblast Growth Factor), and 5 to 3000 µg/mL of vitamin C.

Moreover, the present invention may be a combination of the first aspect, the second aspect, and the third aspect described above. That is, a fourth aspect of the present invention is a method for culturing a mesenchymal stem cell, comprising: a first culture step of culturing a mesenchymal stem cell by suspending mesenchymal stem cells and hematopoietic stem cells in a medium containing blood serum, while maintaining the ratio of mesenchymal stem cells to hematopoietic stem cells within a range of 1:10 to 1:100; and a second culture step of differentiating the mesenchymal stem cell into a biological tissue progenitor cell in a medium containing blood serum at a lower concentration than that in the medium used in the first culture step.

According to the fourth aspect of the present invention, in the first culture step, a mesenchymal stem cell is proliferated to a necessary number of cells in a medium containing a blood serum due to the effect of the blood serum and then in the second culture step, the mesenchymal stem cell is differentiated into a biological tissue progenitor cell in a medium containing blood serum at a lower concentration. After the mesenchymal stem cell proliferates to a necessary number of cells, employment of a medium containing blood serum at a lower concentration can allow the mesenchymal stem cell to differentiate into a biological tissue progenitor cell more efficiently than a case, as conventionally performed, where the cell is cultured using a medium containing blood serum at a similar concentration to that in the medium used for proliferation.

According to the fourth aspect of the present invention, the ratio of mesenchymal stem cells to hematopoietic stem cells is maintained within a range of 1:10 to 1:100. By so doing, it becomes unnecessary to adhere mesenchymal stem cells to the bottom face of a culture vessel, eliminating the necessity of the passage operation so that damage to the mesenchymal stem cell can be reduced, the risk of contamination can be reduced, the culture operation can be simplified so as to shorten the culture period, and proliferation can be efficiently performed so as to thereby reduce the amount of bone marrow collected and alleviate the burden on a patient.

In the fourth aspect of the present invention, the blood serum may be fetal bovine serum, or the blood serum may be human serum.

When fetal bovine serum is used, by setting the concentration of the blood serum in the medium in the second culture step to zero, a biological tissue progenitor cell to be grafted into a living body can be prevented from containing fetal bovine serum.

Moreover, when human serum is used, by reducing the concentration of the blood serum in the medium in the second culture step, the amount of blood serum collected from a patient can be reduced and the burden on the patient can be alleviated.

In the fourth aspect of the present invention, the arrangement may be set such that the ratio of mesenchymal stem cells to hematopoietic stem cells in the medium is monitored so that a liquid factor for increasing the ratio of hematopoietic stem cells is added if the ratio of mesenchymal stem cells to hematopoietic stem cells is more than 1/10.

By so doing, if the ratio of mesenchymal stem cells is increased, the liquid factor can be added to increase the ratio of hematopoietic stem cells so that the mesenchymal stem cells can be efficiently proliferated in a state close to an in vivo state. The monitoring of the ratio of mesenchymal stem cells to hematopoietic stem cells is performed by a flow cytometry (FACS). For example, the number of mesenchymal stem cells is measured with CD29, CD90, or SH3 serving as a cell surface marker, and the number of hematopoietic stem cells is measured with a Stem-kit (BD) by FACS. This enables the ratio of these cells to be monitored.

In this case, the liquid factor for increasing the ratio of hematopoietic stem cells is preferably made from a mixed solution comprising 1 to 100 ng/mL of SCF (Stem Cell Factor), 1 to 50 ng/mL of IL-3 (Interleukin-3), 1 to 50 ng/mL of IL-6, 1 to 50 ng/mL of IL-10, 10 to 300 ng/mL of FL (Flt-3L), and 1 to 50 ng/mL of TPO (Thrombopoietin).

Moreover, in the fourth aspect of the present invention, the arrangement may be also set such that the ratio of mesenchymal stem cells to hematopoietic stem cells in the medium is monitored so that a liquid factor for increasing the ratio of mesenchymal stem cells is added if the ratio of hematopoietic stem cells to mesenchymal stem cells is more than 100.

By so doing, if the ratio of hematopoietic stem cells is increased, the liquid factor can be added to increase the ratio of mesenchymal stem cells so that the mesenchymal stem cells can be efficiently proliferated in a state close to an in vivo state.

In this case, the liquid factor for increasing the ratio of mesenchymal stem cells is preferably made from a mixed solution comprising 1 to 100 ng/mL of PDGF (Platelet-Derived Growth Factor), 1 to 100 ng/mL of bFGF (Basic Fibroblast Growth Factor), and 5 to 3000 µg/mL of vitamin C.

Furthermore, a fifth aspect of the present invention is a method for producing a biological tissue prosthesis in which a mesenchymal stem cell is seeded and cultured in a biological tissue supporting material made from a biocompatible material, in the second culture step of any method for culturing a mesenchymal stem cell according to the fourth aspect described above.

According to the fifth aspect of the present invention, a biological tissue prosthesis having a reduced concentration of contained blood serum can be produced. Moreover, according to the fifth aspect of the present invention, a biological tissue prosthesis can be produced while reducing damage to the mesenchymal stem cell, reducing the risk of contamination, simplifying the culture operation so as to shorten the culture period, and performing efficient proliferation so as to thereby reduce the amount of bone marrow collected and alleviate the burden on a patient.

The present invention demonstrates an effect in which a mesenchymal stem cell can be proliferated to a sufficient degree while reducing the amount of blood serum contained in a biological tissue progenitor cell to be grafted into a living body, and the mesenchymal stem cell can be efficiently differentiated into the biological tissue progenitor cell.

Moreover, the present invention demonstrates an effect in which the passage operation can be eliminated so that damage to the mesenchymal stem cell can be reduced, the risk of contamination can be reduced, the culture operation can be simplified so as to shorten the culture period, and proliferation can be efficiently performed so as to thereby reduce the amount of bone marrow collected and alleviate the burden on a patient.

BEST MODE FOR CARRYING OUT THE INVENTION

First Embodiment

Figure 1:
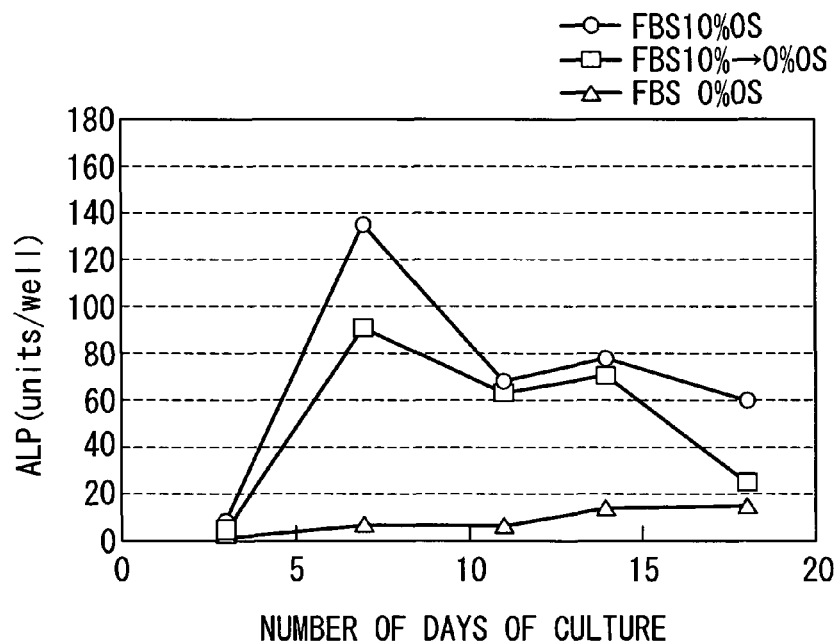
FIG. 1 is a graph showing the measured results of ALP activity in Example of a method for culturing a mesenchymal stem cell according to a first embodiment of the present invention.

Hereunder is a description of a method for culturing a mesenchymal stem cell according to a first embodiment of the present invention.

The method for culturing a mesenchymal stem cell according to the present embodiment comprises a first culture step and a second culture step, in which a mesenchymal stem cell collected from a patient is cultured, and differentiated into a biological tissue progenitor cell, for example, an osteoblast.

The first culture step is a step of placing a mesenchymal stem cell into a first medium containing fetal bovine serum, culturing it under a predetermined culture condition, and thereby proliferating the mesenchymal stem cell to a necessary number of cells.

The second culture step is a step of placing the mesenchymal stem cell cultured in the first culture step into a second medium free from fetal bovine serum and differentiating it into an osteoblast.

According to the method for culturing a mesenchymal stem cell according to the present embodiment, in the first culture step, which takes place in the first medium containing fetal bovine serum, a mesenchymal stem cell can be efficiently proliferated due to the effect of the fetal bovine serum, to quickly achieve a necessary number of cells. In the second culture step, which takes place in the second medium free from fetal bovine serum thereafter, the mesenchymal stem cells are efficiently differentiated into osteoblasts without being interfered by fetal bovine serum.

The medium was removed by washing, and the mesenchymal stem cells that have been proliferated in the first culture step are peeled off from the culture vessel by a proteolytic enzyme such as trypsin, then collected by centrifugation, and placed into the second medium. Accordingly, when the mesenchymal stem cells are placed into the second medium, fetal bovine serum in the first medium that has been adhered to the mesenchymal stem cells is removed, and thus in the second culture step, the mesenchymal stem cells are efficiently differentiated into osteoblasts in the second medium free from fetal bovine serum.

As a result, the osteoblast obtained through the second culture step is not adhered with fetal bovine serum, and can be grafted into the body of a patient as is.

In the present embodiment, the concentration of fetal bovine serum in the second medium is set to zero. However, alternatively, if fetal bovine serum is contained within a range of a concentration higher than zero but lower than the concentration of fetal bovine serum in the first medium, there are an effect of promoting the differentiation induction into an osteoblast, and an effect of reducing the concentration of fetal bovine serum in the osteoblast to be grafted into a patient.

Next is a description of an Example of the method for culturing a mesenchymal stem cell according to the present embodiment.

In the present Example, regarding the first medium, a medium (hereunder, abbreviated as the VFD medium) comprising DMEM (Dulbecco's Modified Eagle Medium), 10% FBS (Fetal Bovine Serum), bFGF (10 ng/mL), vitamin C (50 µg/mL), dexamethasone (10 nM), gentamicin (50 µg/mL), and amphotercin B (0.25 µg/mL) was used as a primary culture medium and as a medium for medium replacement at the first time, and a medium (hereunder, abbreviated as the VF medium) comprising DMEM, 10% FBS, bFGF (10 ng/mL), vitamin C (50 µg/mL), gentamicin (50 µg/mL), and amphotercin B (0.25 µg/mL) was used as a medium for medium replacement from the second time onwards, and as a subculture medium.

As the second medium, a medium (hereunder, abbreviated as the FBS 0% OS medium) comprising DMEM, vitamin C (50 µg/mL), dexamethasone ($10^{-7}$ M), β-glycerophosphate (β-GP) (10 mM), gentamicin (50 µg/mL), and amphotercin B (0.25 µg/mL) was used.

As a Comparative Example, a case using a medium (hereunder, abbreviated as the FBS 10% OS medium) comprising DMEM, 10% FBS, vitamin C (50 µg/mL), dexamethasone ($10^{-7}$ M), β-GP (10 mM), gentamicin (50 µg/mL), and amphotercin B (0.25 µg/mL), was examined.

The first culture step was performed by the following procedure.

1. The bone marrow fluid collected from a patient is centrifuged using a centrifugal machine (1500 rpm, 5 minutes), and the supernatant is removed.

2. The bone marrow solution is well mixed using a pipette and is transferred into a 150 mL storage bottle. A VFD medium is added thereto to make the volume 120 mL.

3. The mixture is stirred by pipetting, and 15 mL of the mixture is respectively dispensed into eight 75 cm² flasks. The caps of these flasks are closed.

4. The flasks are placed in a $CO_2$ incubator, whose temperature has been set at 37° C., followed by culturing for 3 to 4 days.

5. 10.5 mL (70%) of the medium in the flask is respectively removed, and 10.5 mL of a fresh VFD medium is added to thereby perform the medium replacement at the first time.

6. The flasks are placed in a $CO_2$ incubator, whose temperature has been set at 37° C., followed by culturing for 3 to 4 days.

7. 15 mL (total volume) of the medium in the flask is respectively removed, and 15 mL of a fresh VF medium is added to thereby perform the medium replacement at the second time.

8. The flasks are placed in a $CO_2$ incubator, whose temperature was set at 37° C., followed by repetition of culturing for 3 to 4 days and medium replacement.

The second culture step is performed at the time when the necessary number of cells is attained in the first culture step.

The second culture step was performed by the following procedure.

1. After the medium in the flask is removed and washed off, the mesenchymal stem cells obtained in the first culture step are peeled off by a trypsin solution, and collected by centrifugation. Then, these cells are placed into the second medium to make a cell suspension.

2. The cells are seeded at a cell density of $1\times10^4$ cells/cm$^2$. in a 12-well plate so as to make a medium volume of 2 mL/well.

3. The plate is placed in a $CO_2$ incubator, whose temperature has been set at 37° C., followed by culturing and medium replacement every 3 to 4 days.

In this case, in order to observe the influence of fetal bovine serum on the mesenchymal stem cell after adhesion, in the second culture step using the FBS 0% OS medium, examination was performed for two cases: a case where the FBS 10% OS medium was used to adhere the mesenchymal stem cell for about four hours at the initial stage of culture, and then was replaced with the FBS 0% OS medium; and a case where the FBS 10% OS medium was used at the beginning of the second culture step, and was replaced with the FBS 0% OS medium on the 7th day of the culture.

Moreover, a conventional case where the FBS 10% OS medium was continuously used from the beginning of the second culture step is shown as a Comparative Example.

The analysis was performed by ALP activity measurement, DNA concentration measurement, and calcium concentration measurement.

The ALP activity measurement was performed by the following procedure.

1. The obtained cells are washed with a physiological saline solution three times.
2. 400 µL/well of 0.2% Triton is added.
3. The cells are peeled off with a cell scraper.
4. The whole cells are collected.
5. The cells are crushed with a homogenizer.
6. The resultant solution is centrifuged (8000 rpm, 5 minutes), and the supernatant is used as the sample.
7. The ALP activity is measured using an ALP activity measurement kit (LabAssay ALP: manufactured by Wako Pure Chemical industries, Ltd.).

The DNA concentration measurement was performed by the following procedure.

1. The obtained cells are washed with a physiological saline solution three times.
2. 400 µL/well of 0.2% Triton is added.
3. The cells are peeled off with a cell scraper.
4. The whole cells are collected.
5. The cells are crushed with a homogenizer.
6. The resultant solution is centrifuged (8000 rpm, 5 minutes), and the supernatant is used as the sample.
7. The DNA concentration is measured using a DNA concentration measurement kit (Fluorescent DNA Quantitation Kit: manufactured by BIO-RAD Laboratories, Inc.).

The calcium concentration measurement was performed by the following procedure.

1. The obtained cells are washed with a physiological saline solution three times.
2. 400 µL/well of 0.2% Triton is added, and extraction is performed at a room temperature for 180 minutes.
3. The respective sample is collected, and the calcium concentration thereof is measured using a calcium concentration measurement kit (calcium C-test Wako: manufactured by Wako Pure Chemical industries, Ltd.).

FIG. 1 shows the measured results of ALP activity.

According to this, in the cases where the FBS 10% OS medium was used from the beginning of the second culture step, it was found that the ALP activity was changed in similar patterns in both cases: the case where the culture was performed continuously in the FBS 10% OS medium as was; and the case where the medium was replaced with the FBS 0% OS medium on the 7th day from the beginning. On the other hand, in the case where the FBS 0% OS medium was used from the beginning of the second culture step, it was found that the ALP activity was low overall.

Figure 2:
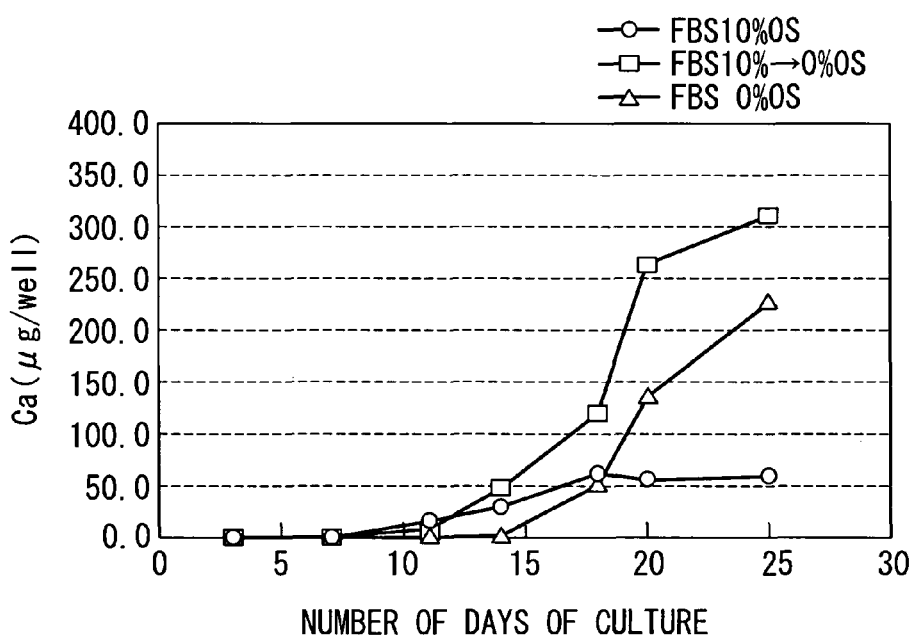
FIG. 2 is a graph showing the measured results of calcium concentration in Example of the method for culturing a mesenchymal stem cell according to the first embodiment of the present invention.

FIG. 2 shows the measured results of calcium concentration.

According to this, in the case of a conventional culture method where the FBS 10% OS medium was used from the beginning of the second culture step and the culture was performed continuously in the FBS 10% OS medium as was, it was found that the calcium accumulation was saturated with the passage of culture time. On the other hand, in both cases: the case where the FBS 10% OS medium was replaced with the FBS 0% OS medium on the 7th day from the beginning of the second culture step; and the case of the present embodiment where the FBS 0% OS medium was used from the beginning of the second culture step, it was found that the calcium accumulation was greatly increased compared to the conventional culture method, with the passage of culture period.

Figure 3:
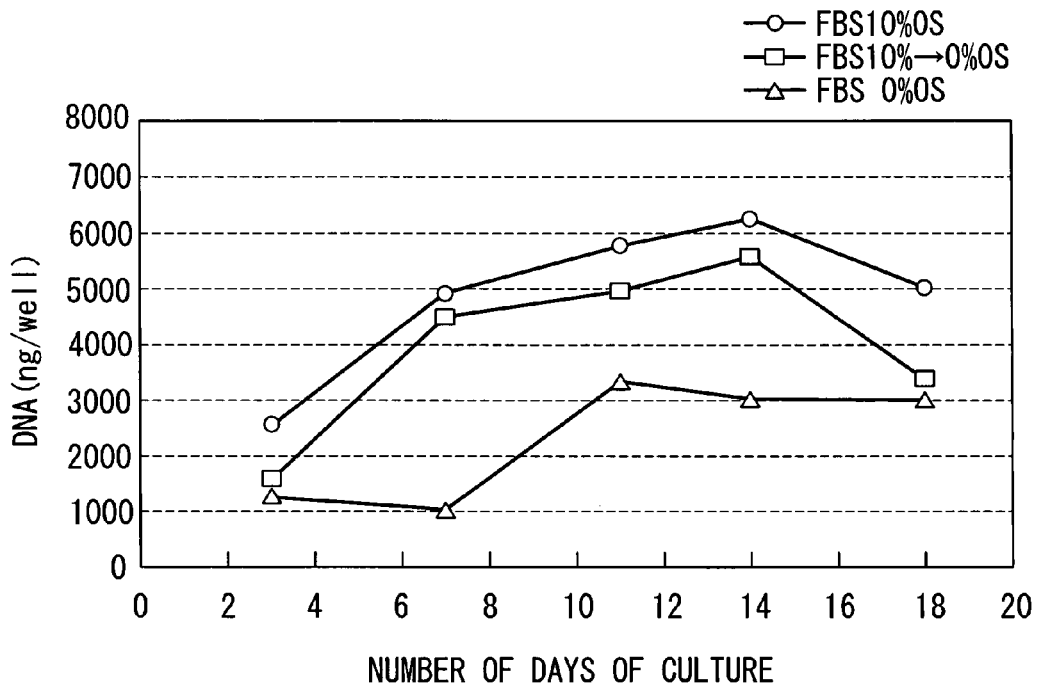
FIG. 3 is a graph showing the measured results of DNA concentration in Example of the method for culturing a mesenchymal stem cell according to the first embodiment of the present invention.

FIG. 3 shows the measured results of DNA concentration.

According to this, in the cases where the FBS 10% OS medium was used from the beginning of the second culture step, it was found that the DNA concentration was changed in similar patterns in both cases: the case where the culture was performed continuously in the FBS 10% OS medium as was; and the case where the medium was replaced with the FBS 0% OS medium on the 7th day from the beginning. On the other hand, in the case where the FBS 0% OS medium was used from the beginning of the second culture step, it was found that the DNA concentration was low overall.

It was found from the measured results of DNA concentration that the speed of cell proliferation differed according to the conditions of use of fetal bovine serum. Therefore, in order to accurately compare the ALP activity and the calcium accumulation, the ALP activity and the calcium accumulation per cell were obtained by dividing the measured results of the ALP activity of FIG. 1 and the calcium concentration of FIG. 2 by the measured results of DNA concentration of FIG. 3, which are respectively shown in FIG. 4 and FIG. 5.

Figure 4:
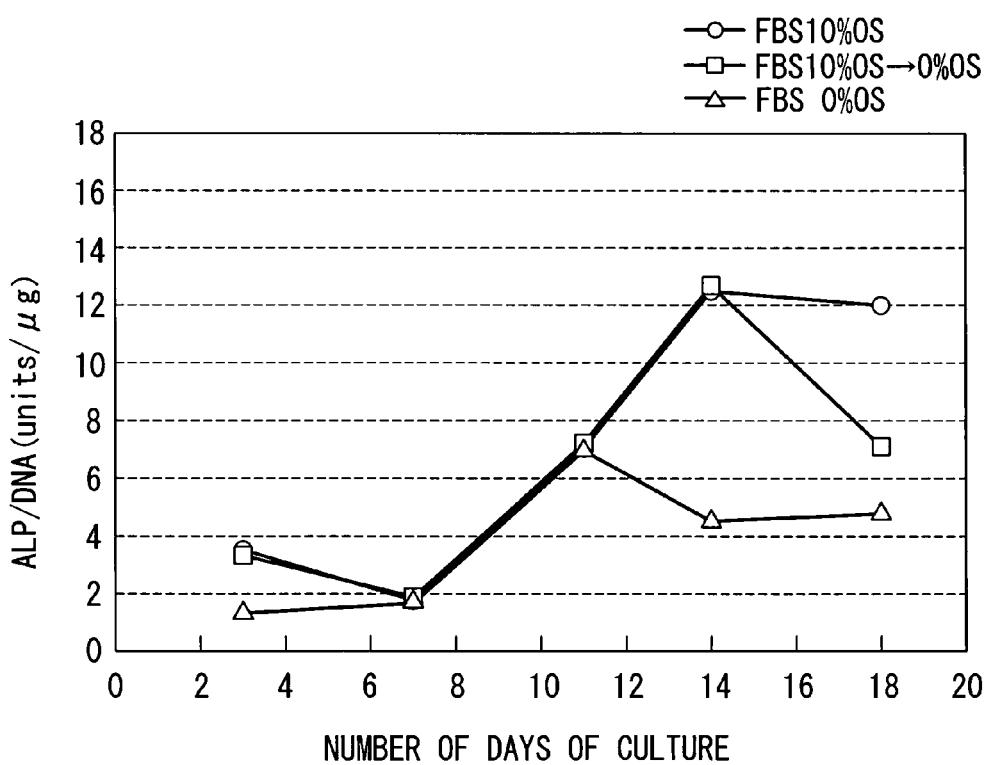
FIG. 4 is a graph showing the ALP activity per DNA obtained by correcting the ALP activity of FIG. 1 by the DNA concentration of FIG. 3.

As shown in FIG. 4, according to the ALP activity corrected by the DNA concentration, in both cases: the case where the FBS 0% OS medium was used from the beginning of the second culture step; and the case where the medium was replaced with the FBS 0% OS medium from the 7th day of the culture, the ALP activity was increased in the same tendency up to the 11th day, compared to the conventional case where the FBS 10% OS medium was used. Moreover, the ALP activity corrected by the DNA concentration was changed according to the conditions of fetal bovine serum thereafter.

As compared with FIG. 1, the ALP activity in the FBS 0% OS medium corrected by the DNA concentration was increased, and was the same as those in the other conditions up to the 11th day. After the 11th day, although the ALP activity was lower than those in the other conditions, it was kept at a fixed level, which is considered to contribute to the following calcium accumulation (calcification).

Figure 5:
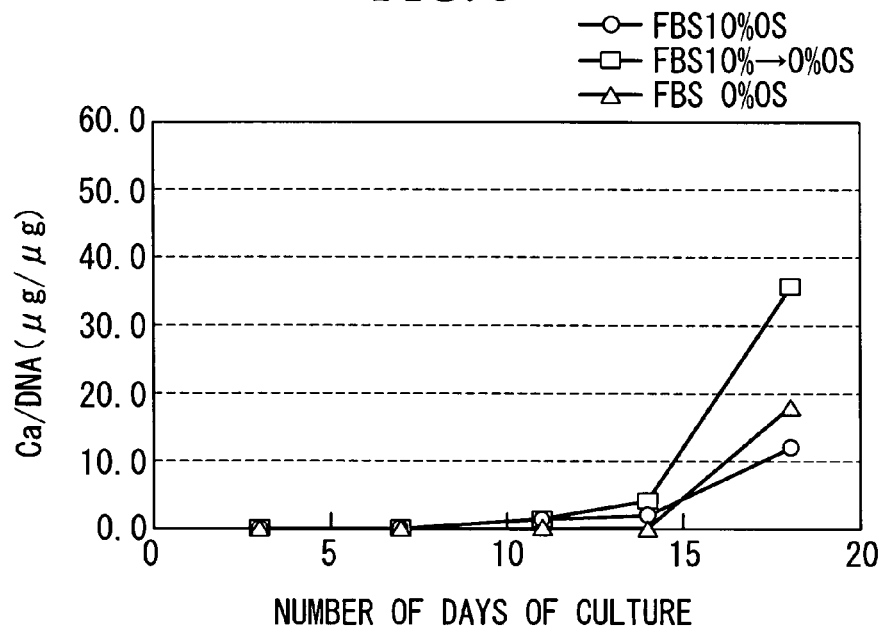
FIG. 5 is a graph showing the measured results of calcium concentration per cell obtained by correcting the measured results of calcium concentration of FIG. 2 by the DNA concentration of FIG. 3.

FIG. 5 shows the calcium concentration corrected by the DNA concentration.

According to this, in both cases: the case where the FBS 0% OS medium was used from the beginning of the second culture step; and the case where the medium was replaced with the FBS 0% OS medium from the 7th day from the beginning, it was found that the calcium accumulation per cell was greatly increased compared to the conventional culture method using the FBS 10% OS medium, with the passage of culture time.

From the above results, replacement of the medium with a serum-free medium which does not contain bovine serum at the time of differentiation induction of a mesenchymal stem cell into an osteoblast, can efficiently provide osteoblasts of the equivalent amount or more as compared to the conventional culture method where bovine serum is continuously used. Furthermore, since the content of bovine serum in the obtained osteoblast can be reduced, this method is preferable. In particular, as the culture time is elongated, more osteoblasts can be obtained.

Therefore, according to the method for producing a cultured bone in which a mesenchymal stem cell is seeded and cultured in a biological tissue supporting material made from a biocompatible material, for example, a porous calcium phosphate material such as a porous β-tricalcium phosphate material, in the second culture step, a cultured bone free from bovine serum can be efficiently produced.

Second Embodiment

Next is a description of a method for culturing a mesenchymal stem cell according to a second embodiment of the present invention.

The method for culturing a mesenchymal stem cell according to the present embodiment assumes cases where human autologous serum is used. In the first embodiment, since fetal bovine serum was used, a method in which the fetal bovine serum concentration was shifted to zero in the second culture step was taken with the object of removing fetal bovine serum. However, in the cases where human autologous serum is used, it is not necessary to make the concentration zero. Conversely, from the viewpoint in which the existence of the blood serum is rather effective for cell proliferation, it has been considered that the blood serum is preferably left remaining. Therefore, the level of blood serum concentration at which the cell proliferation and differentiation are not influenced, was examined.

According to the method for culturing a mesenchymal stem cell according to the present embodiment, in the first culture step, which takes place in the first medium containing 10 to 15% human autologous serum, a mesenchymal stem cell is efficiently proliferated due to the high concentration of the autologous serum. As a result, the necessary number of cells of mesenchymal stem cells can be quickly achieved. In the second culture step, which takes place in the second medium containing a low concentration of autologous serum thereafter, the mesenchymal stem cells are differentiated into osteoblasts while maintaining the number of mesenchymal stem cells.

The medium was removed by washing, and the mesenchymal stem cells that have been proliferated in the first culture step are peeled off from the culture vessel by a proteolytic enzyme such as trypsin, then collected by centrifugation, and placed into the second medium. In the second culture step, the mesenchymal stem cells are efficiently differentiated into osteoblasts in the second medium of a low human serum concentration.

As a result, the amount of human serum collected to be used in the second culture step can be reduced, providing an advantage in that the burden on a patient can be alleviated.

Moreover, in the present embodiment, the human serum concentration in the second medium was set lower than the human serum concentration in the first medium within the range of a concentration higher than zero, and thus the osteoblast to be finally grafted into a patient contains the human serum, which is, however, not a problem since the human serum used is collected from the same patient serving as the source of the mesenchymal stem cell.

Conversely, the human serum may be rather preferably contained in the second medium within the range of a concentration higher than zero, in some cases. That is, in the second culture step, it becomes possible to continuously provide osteoblasts, not by completely differentiating mesenchymal stem cells into osteoblasts, but by differentiating a part of the mesenchymal stem cells into osteoblasts while proliferating the other part of the mesenchymal stem cells. Accordingly, for the purpose requiring the continuous provision of osteoblasts, the human serum is preferably contained in the second medium within the range of a concentration higher than zero.

Next is a description of an Example of the method for culturing a mesenchymal stem cell according to the present embodiment.

In the present Example, two types of mesenchymal stem cells A, and B are used.

The first medium is the same as the first medium of the first embodiment except for that 15% human autologous serum was used instead of 10% FBS.

As the second medium, two types of media: a medium (hereunder, abbreviated as the HS 5% OS medium) comprising DMEM, 5% human serum, vitamin C (50 μg/mL), dexamethasone ($10^{-7}$M), β-GP (10 mM), gentamicin (50 μg/mL), and amphotercin B (0.25 μg/mL); and a HS 10% OS medium having 10% human serum concentration, were prepared. Moreover, as a Comparative Example, a conventional HS 15% OS medium having 15% human serum concentration was prepared.

The first culture step and the second culture step were the same as those of the first embodiment.

However, in the second culture step, three types of second media having different human autologous serum concentrations were continuously used.

The method for measuring the ALP activity, the method for measuring the calcium concentration, and the method for measuring the DNA concentration were the same as described above.

Figure 6:
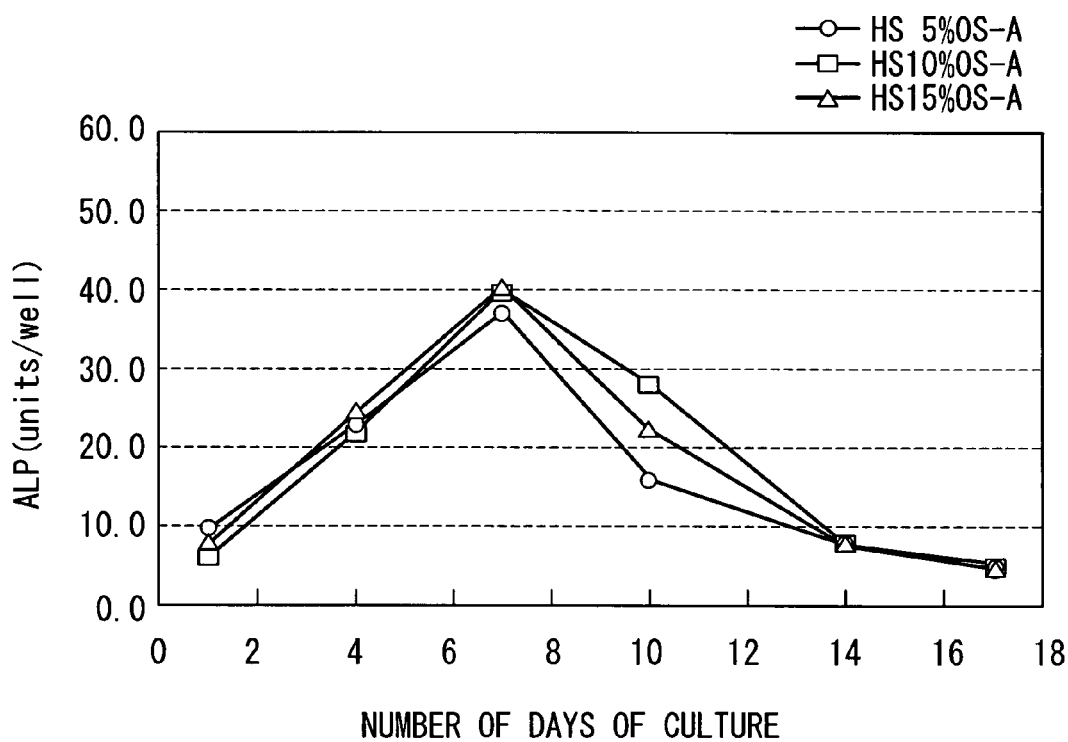
FIG. 6 is a graph showing the measured results of ALP activity in Example of the method for culturing a mesenchymal stem cell according to a second embodiment of the present invention.
Figure 7:
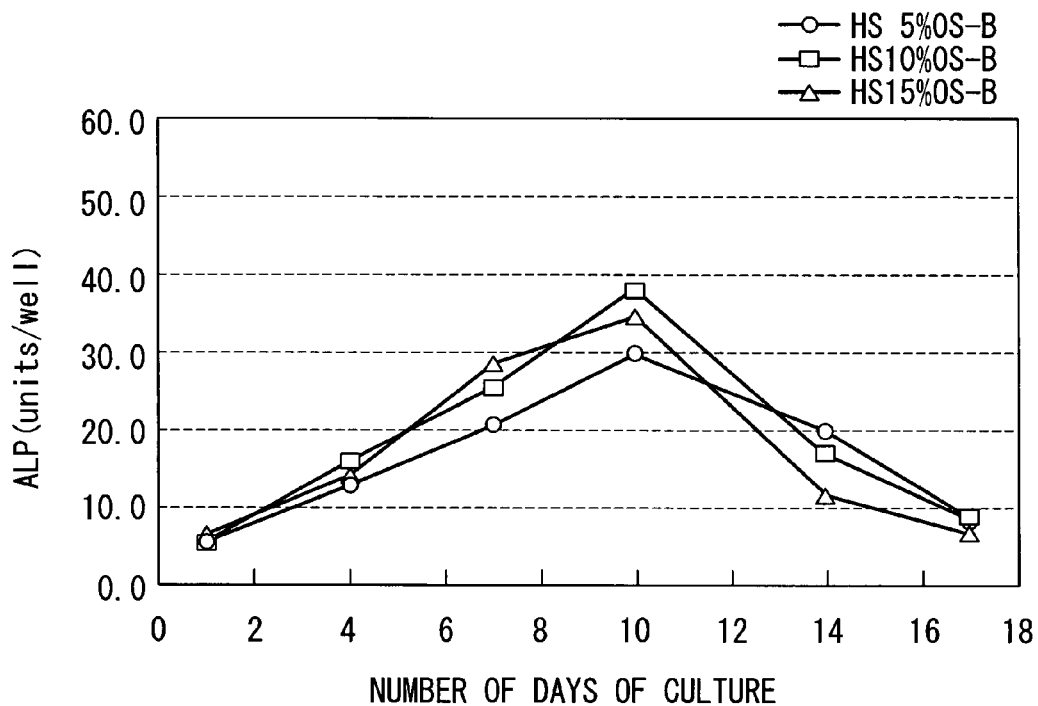
FIG. 7 is a graph showing the measured results of ALP activity in another Example of the method for culturing a mesenchymal stem cell according to the second embodiment of the present invention.
Figure 8:
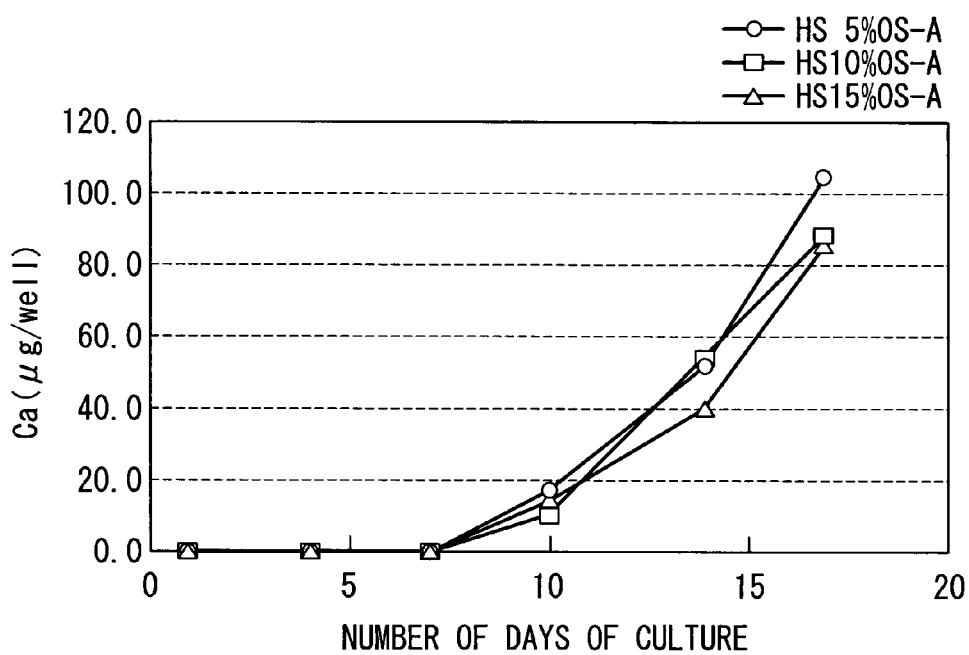
FIG. 8 is a graph showing the measured results of calcium concentration in Example of the method for culturing a mesenchymal stem cell according to the second embodiment of the present invention.
Figure 9:
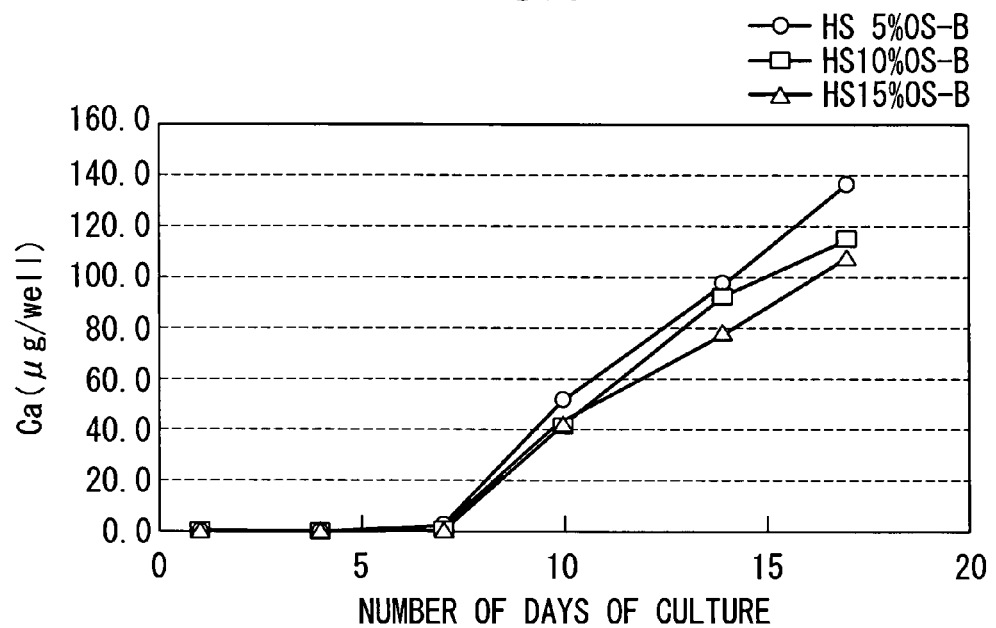
FIG. 9 is a graph showing the measured results of calcium concentration in another Example of the method for culturing a mesenchymal stem cell according to the second embodiment of the present invention.
Figure 10:
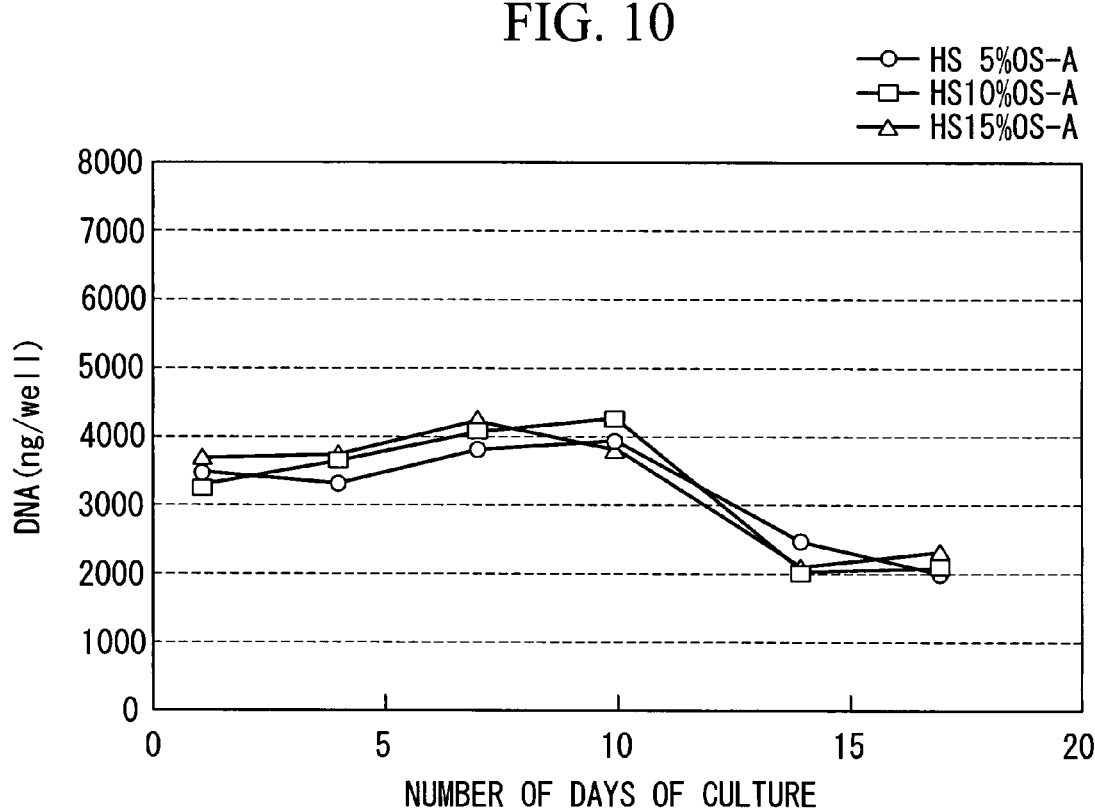
FIG. 10 is a graph showing the measured results of DNA concentration in Example of the method for culturing a mesenchymal stem cell according to the second embodiment of the present invention.
Figure 11:
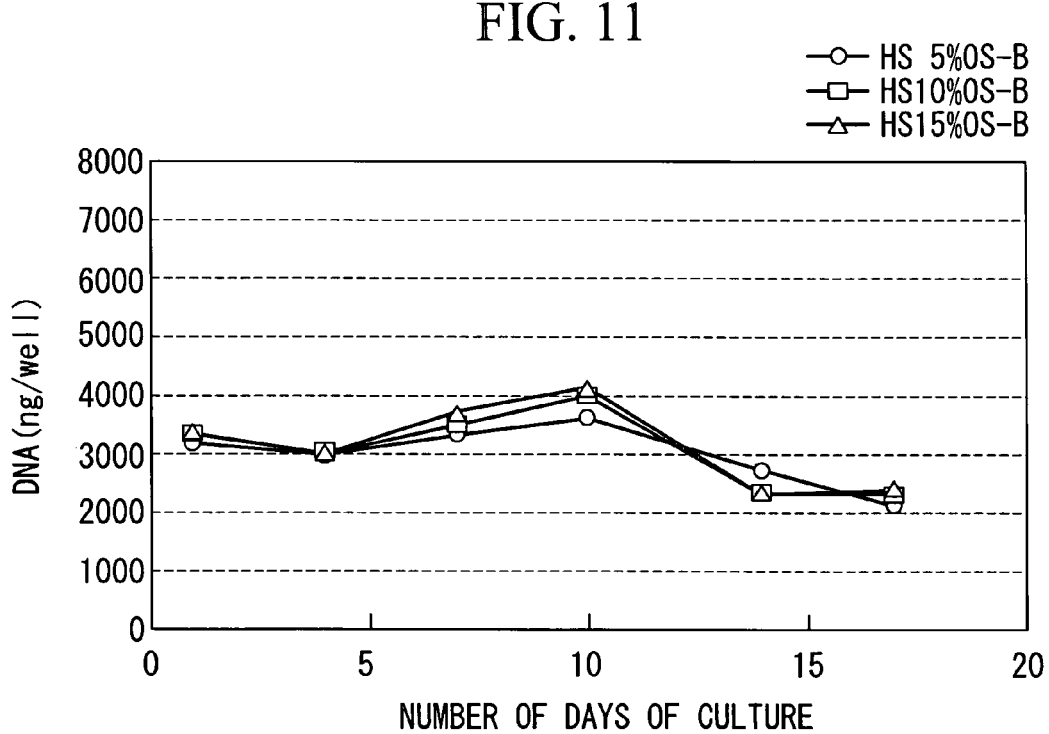
FIG. 11 is a graph showing the measured results of DNA concentration in another Example of the method for culturing a mesenchymal stem cell according to the second embodiment of the present invention.

FIG. 6, FIG. 8, and FIG. 10 show the measured results of ALP activity, the measured results of calcium concentration, and the measured results of DNA concentration of the mesenchymal stem cell A. FIG. 7, FIG. 9, and FIG. 11 show the measured results of ALP activity, the measured results of calcium concentration, and the measured results of DNA concentration of the mesenchymal stem cell B.

According to FIG. 6 through FIG. 11, in both cases of the mesenchymal stem cells A and B, it was found that the ALP activity, the calcium concentration, and the DNA concentration showed substantially same tendencies regardless of the human serum concentration in the second medium.

That is, a relatively high concentration of human serum is required in the first culture step of proliferating a mesenchymal stem cell, and a medium containing human serum at a similar concentration has been conventionally used as well in the second culture step. However, according to the method for culturing a mesenchymal stem cell according to the present embodiment, an equivalent amount of osteoblasts as compared with the conventional case can be obtained using a smaller amount of human serum. Accordingly, there is an effect in which an equivalent amount of osteoblasts as compared with the conventional case can be obtained while reducing the amount of human serum collected from a patient and greatly alleviating the burden on the patient.

Moreover, in cases where a cultured bone is produced using the method for culturing a mesenchymal stem cell according to the present embodiment, similarly to the above, a cultured bone equivalent to that of the conventional case can be efficiently produced with a small amount of human serum.

In the above respective embodiments, the description was about the case where the differentiation from a mesenchymal stem cell into an osteoblast was induced in the second culture step, which is however not to be considered as limiting. The present invention may be applied to differentiation induction into any other biological tissue progenitor cell. Similarly, the biological tissue prosthesis is not to be limited to the cultured bone, and the present invention may be applied to the production of any other biological tissue prosthesis.

Moreover, in the above embodiments, the description was about the case where the human serum concentration was reduced within the range of a concentration higher than zero. However, a predetermined effect is expected to be obtainable even if the human serum concentration in the second medium is set to zero instead of the above case.

Third Embodiment

Next is a description of a method for culturing a mesenchymal stem cell according to a third embodiment of the present invention.

In the method for culturing a mesenchymal stem cell according to the present embodiment, firstly, bone marrow fluid collected from a patient is placed into a medium stored in a culture vessel, and the mixture is stirred while keeping the temperature at 37° C. The inner wall of the culture vessel was coated so as not to be adhered with an adhesive mesenchymal stem cell.

In the bone marrow fluid collected from the patient, mesenchymal stem cells and hematopoietic stem cells are present at a proportion of 1:10 to 1:100. Accordingly, at the time of beginning of culture when the bone marrow fluid is placed, the ratio of mesenchymal stem cells to hematopoietic stem cells in the culture vessel is in a state close to an in vivo state. Moreover, stirring of the medium in the culture vessel makes the mesenchymal stem cells and the hematopoietic stem cells suspended in the medium, and furthermore the inner wall of the culture vessel is coated to prevent the adhesion of the adhesive mesenchymal stem cell. Therefore, the mesenchymal stem cells are kept in a suspended state in the medium. This state is also close to an in vivo state.

In the method for culturing a mesenchymal stem cell according to the present embodiment, the ratio of mesenchymal stem cells to hematopoietic stem cells in the medium is monitored. For example, the number of mesenchymal stem cells and the number of hematopoietic stem cells in the culture can be monitored by measuring the number of mesenchymal stem cells with CD29, CD90, or SH3 serving as a cell surface marker, and the number of hematopoietic stem cells with a Stem-kit (BD) by FACS. When the number of hematopoietic stem cells in the medium is increased, a liquid factor for increasing the number of mesenchymal stem cells is added. When the number of hematopoietic stem cells in the medium is decreased, a liquid factor for increasing the number of hematopoietic stem cells is added.

Examples of the liquid factor for increasing the number of mesenchymal stem cells may include a mixed solution comprising 1 to 100 ng/mL of PDGF (Platelet-Derived Growth Factor), 1 to 100 ng/mL of bFGF (Basic Fibroblast Growth Factor), and 5 to 3000 µg/mL of vitamin C. Moreover, examples of the liquid factor for increasing the number of hematopoietic stem cells may include a mixed solution comprising 1 to 100 ng/mL of SCF (Stem Cell Factor), 1 to 50 ng/mL of IL-3 (Interleukin-3), 1 to 50 ng/mL of IL-6, 1 to 50 ng/mL of IL-10, 10 to 300 ng/mL of FL (Flt-3L), and 1 to 50 ng/mL of TPO (Thrombopoietin).

In this manner, according to the method for culturing a mesenchymal stem cell according to the present embodiment, the ratio of mesenchymal stem cells to hematopoietic stem cells in the medium during the culture can be kept in a state close to an in vivo state at all times, therefore the mesenchymal stem cells can be efficiently proliferated similarly to the in vivo state, while keeping the mesenchymal stem cells suspended in a similar manner to the in vivo state without being adhered onto the culture vessel.

That is, according to the culture method according to the present embodiment, a mesenchymal stem is cultured while being kept suspended without being adhered onto the culture vessel, thus eliminating the necessity of the passage operation in which the culture vessel has to be replaced, and providing advantages in that concerns involved in the passage operation, that is, damage to the mesenchymal stem cell, and the risk of contamination can be reduced.

Moreover, by eliminating the necessity of the passage operation which requires time and effort, the culture operation can be simplified, and the culture period can be shortened, so that a mesenchymal stem cell can be efficiently proliferated to a necessary number of cells quickly.

Furthermore, since a mesenchymal stem cell is efficiently proliferated in a state similar to an in vivo state, the amount of bone marrow fluid collected can be reduced, thus providing an advantage in that the burden on a patient can be alleviated.

Figure 12:
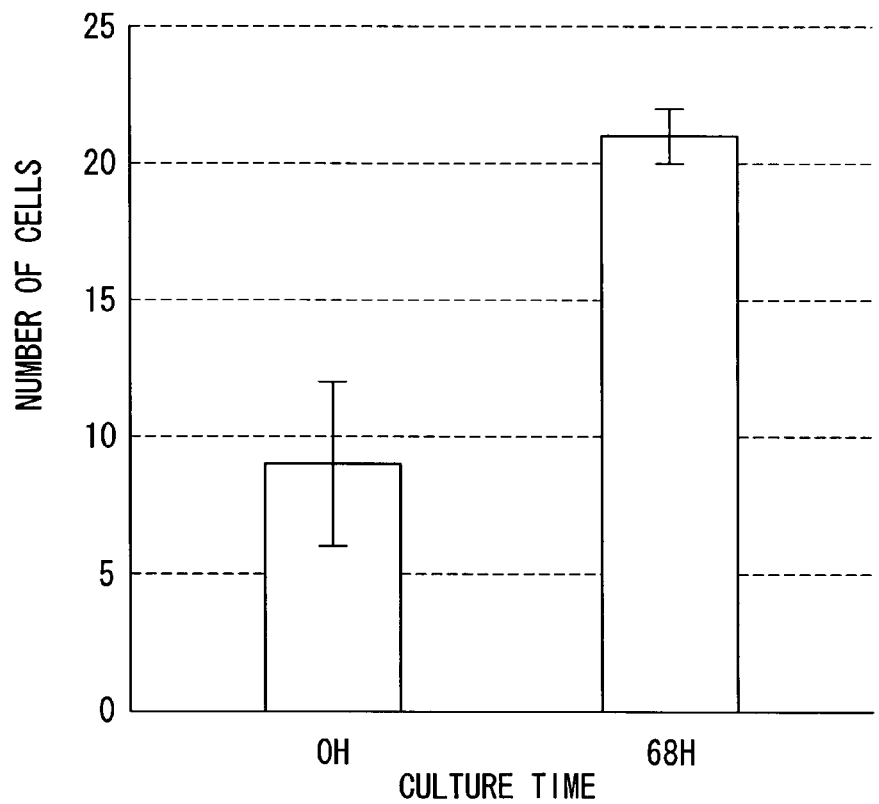
FIG. 12 is a graph showing the result of culture by the method for culturing a mesenchymal stem cell according to a third embodiment of the present invention.

Table 1 and FIG. 12 show the result of suspension culture by maintaining the ratio of mesenchymal stem cells to hematopoietic stem cells within a state similar to an in vivo state. Specifically, bone marrow fluid containing 125 U/mL of heparin was cultured in an incubator at 37° C., resulting in a 2.3 times increase in the number of proliferated mesenchymal stem cells after 68 hours as compared to the initial state. As a result, it was found that, a mesenchymal stem cell can be proliferated even in the suspended state by maintaining the ratio of respective cells in the bone marrow, in particular the ratio of mesenchymal stem cells to hematopoietic stem cells, within a state similar to an in vivo state.

TABLE 1

| CULTURE TIME | NUMBER OF CELLS/WELL | | | MEAN VALUE | STANDARD DEVIATION |
| --- | --- | --- | --- | --- | --- |
| | 1 | 2 | 3 | | |
| 0 H | 6 | 11 | 10 | 9 | 3 |
| 68 H | 18 | 22 | 22 | 21 | 2 |

The invention claimed is:

1. A method for culturing a mesenchymal stem cell, comprising:
   a first culture step of culturing a mesenchymal stem cell by suspending mesenchymal stem cells and hematopoietic stem cells in a medium containing blood serum, while maintaining the ratio of mesenchymal stem cells to hematopoietic stem cells within a range of 1:10 to 1:100; and
   a second culture step of differentiating the mesenchymal stem cell into a biological tissue progenitor cell in a medium containing blood serum at a lower concentration than that in the medium used in the first culture step, wherein
   the ratio of mesenchymal stem cells to hematopoietic stem cells in a medium is monitored, and a liquid factor for increasing the ratio of mesenchymal stem cells is added if the ratio of hematopoietic stem cells to mesenchymal stem cells is more than 100, and the liquid factor for increasing the ratio of mesenchymal stem cells is made from a mixed solution comprising 1 to 100 ng/mL of PDGF, 1 to 100 ng/mL of bFGF, and 5 to 3000 μg/mL of vitamin C.

2. A method for culturing a mesenchymal stem cell according to claim 1, wherein the concentration of blood serum in the medium in the second culture step is approximately zero.

3. A method for culturing a mesenchymal stem cell according to claim 1, wherein the concentration of blood serum in the medium in the second culture step is higher than zero.

4. A method for culturing a mesenchymal stem cell according to claim 2, wherein the blood serum is fetal bovine serum.

5. A method for culturing a mesenchymal stem cell according to claim 1, wherein the blood serum is human serum.

6. A method for culturing a mesenchymal stem cell according to claim 1, wherein the ratio of mesenchymal stem cells to hematopoietic stem cells in a medium is monitored, and a liquid factor for increasing the ratio of hematopoietic stem cells is added if the ratio of mesenchymal stem cells to hematopoietic stem cells is more than 1/10.

7. A method for culturing a mesenchymal stem cell according to claim 6, wherein the liquid factor for increasing the ratio of hematopoietic stem cells is made from a mixed solution comprising 1 to 100 ng/mL of SCF, 1 to 50 ng/mL of IL-3, 1 to 50 ng/mL of IL-6, 1 to 50 ng/mL of IL-10, 10 to 300 ng/mL of FL, and 1 to 50 ng/mL of TPO.

8. A method for producing a biological tissue prosthesis, comprising culturing a mesenchymal stem cell according to the method for culturing of any one of claim 1 to claim 7, wherein in the second culture step of said method for culturing, the mesenchymal stem cell is seeded and cultured in a biological tissue supporting material made from a biocompatible material.

* * * * *